(12) United States Patent
Bruun et al.

(10) Patent No.: US 9,224,200 B2
(45) Date of Patent: Dec. 29, 2015

(54) **COMPUTER VISION BASED METHOD FOR EXTRACTING FEATURES RELATING TO THE DEVELOPMENTAL STAGES OF *TRICHURIS* SPP. EGGS**

(71) Applicant: Parasite Technologies A/S, Rungsted Kyst (DK)

(72) Inventors: Johan Musaeus Bruun, København Ø (DK); Jens Michael Carstensen, Bjæverskov (DK); Christian Moliin Outzen Kapel, Rungsted Kyst (DK)

(73) Assignee: Parasite Technologies A/S, Rungsted Kyst (DK)

( * ) Notice: Subject to any disclaimer, the term of this patent is extended or adjusted under 35 U.S.C. 154(b) by 46 days.

(21) Appl. No.: 13/796,660

(22) Filed: Mar. 12, 2013

(65) Prior Publication Data

US 2013/0287252 A1    Oct. 31, 2013

Related U.S. Application Data

(60) Provisional application No. 61/639,229, filed on Apr. 27, 2012.

(51) Int. Cl.
*G06T 7/00* (2006.01)
*G06K 9/00* (2006.01)
*A61K 35/62* (2006.01)

(52) U.S. Cl.
CPC .......... *G06T 7/0012* (2013.01); *G06K 9/00147* (2013.01); *A61K 35/62* (2013.01)

(58) Field of Classification Search
CPC .......... G06K 9/00127; G06K 9/00147; G06T 7/0012; G06T 7/0042; G06T 7/0051; G06T 7/60; G06T 2207/10056; G06T 2207/30024; A61K 35/62
USPC ................. 382/100, 128, 133, 199, 203, 227; 356/39, 625, 634, 635; 348/79
See application file for complete search history.

(56) References Cited

U.S. PATENT DOCUMENTS

| | | | |
|---|---|---|---|
| 7,771,923 B2 | 8/2010 | Abromeit | 435/4 |
| 7,833,537 B2 | 11/2010 | Weinstock et al. | 424/265.1 |
| 7,951,547 B2 | 5/2011 | Elsemore et al. | 435/7.1 |
| 8,105,795 B2 | 1/2012 | Elsemore et al. | 435/7.22 |
| 2011/0191869 A1 | 8/2011 | Tewes et al. | 800/8 |

FOREIGN PATENT DOCUMENTS

WO    WO9963057 A1    12/1999    ............... C12N 5/00

OTHER PUBLICATIONS

Summers, et al., *Trichuris suis* Therapy in Crohn's Disease, 54 Gut 87 (2005).

(Continued)

*Primary Examiner* — Andrew W Johns
(74) *Attorney, Agent, or Firm* — K. David Crockett, Esq.; Niky Economy Syrengelas, Esq.; Crockett & Crockett, PC

(57) ABSTRACT

There is provided a computer vision based method for extracting features relating to the developmental stages of *Trichuris* spp. eggs, wherein for the final developmental stages a larva is present inside the egg, said *Trichuris* spp. eggs having a substantially oblong or elliptical shape with a protruding polar plug at each end, the shape of the *Trichuris* spp. eggs thereby defining a longitudinal direction and a transverse direction of the eggs.

42 Claims, 13 Drawing Sheets

(56) References Cited

OTHER PUBLICATIONS

Summers, et al., *Trichuris suis* Therapy for Active Ulcerative Colitis: A Randomized Controlled Trial, 128 Gastroenterology 825 (2005).
Reddy, et al., The Use of *Trichuris suis* and other Helminth Therapies to Treat Crohn's Disease, 100 Parasitol Research 921 (2007).
Yang, et al., Automatic Identification of Human Helminth Eggs on Microscopic Fecal Specimens Using Digital Image Processing and an Artificial Neural Network, 48 IEEE Transaction on Biomedical Engineering 718 (IEEE 2001).
Avci, et al., An Expert Diagnosis System for Classification of Human Parasite Eggs Based on Multi-Class SVM, 36 Expert Systems with Applications 43 (2009).
Dogantekin, et al., A Robust Technique Based on Invariant Moments—ANFIS for Recognition of Human Parasite Eggs in Microscopic Images, 35 Expert Systems with Applications 728 (2008).
Thienpoint, et al., Diagnosing Helminthiasis by Coprological Examination, 48 (1986).
Roberts, et al., Nematodes: *Trichurida* and Dioctophymatida, Enoplean Parasites, Foundations of Parasitology, Seventh Edition 397 (2005).
Pittman, et al., *Trichuris suis* in Finishing Pigs: Case Report and Review, Journal of Swine Health and Production 306 (2010).
Abramowitz, et al., Darkfield Illumination, Olympus Microscopy Resource Center (Apr. 26, 2012) http://www.olympusmicro.com/primer/techniques/dark.
Beer, Morphological Descriptions of the Egg and Larval Stages of *Trichuris suis* Schrank, 1788, Parasitology 263 (1973).
Black, et al., Survival Rates of Parasite Eggs in Sludge During Aerobic and Anaerobic Digestion, Applied and Environmental Microbiology 1138 (1982).
Otsu, A Threshold Selection Method from Gray-Level Histograms, IEEE Transactions on Systems, Man, and Cybernetics 62 (IEEE 1979).
Dillencourt, et al., A General Approach to Connected-Component Labeling for Arbitrary Image Representations, vol. 39 Journal of the Assocation for Computing Machinery 253 (1992).
Measure Properties of Image Regions, MATLAB Regionprops (Apr. 26, 2012) http://www.mathworks.se/help/toolbox/images/ref/regionprops.html.
Berge, et al., Improved Red Blood Cell Counting in Thin Blood Smears, 204 (2011).
Diaz, et al., Automatic Clump Splitting for Cell Quantification in Microscopical Images, Proceedings of the Congress on Pattern Recognition 12th Iberoamerican Conference on Progress in Pattern Recognition, Image Analysis and Applications 1 (2007).
Witkin, Scale-Space Filtering: A New Approach to Multi-Scale Description, IEEE International Conference on ICASSP 150 (IEEE 1984).
Burt, et al., The Laplacian Pyramid as a Compact Image Code, IEEE Transactions on Communications 532 (IEEE 1983).
Mallat, A Theory for Multiresolution Signal Decomposition: The Wavelet Representation, IEEE Transactions on Pattern Analysis and Machine Intelligence 674 (IEEE 1989).
Canny, A Computational Approach to Edge Detection, IEEE Transactions on Pattern Analysis and Machine Intelligence 679 (IEEE 1986).
Gonzalez, et al., Digital Image Processing, International Edition 706 (2008).
Bruun, et al., Classification of Parasite Eggs Used as an Active Pharmaceutical Ingredient (API), Danish Society for Parasiteology 7 (2012).
Suzuki, et al., Automatic Segmentation and Classification of Human Intestinal Parasites from Microscopy Images, IEEE Transactions on Biomedical Engineering 1 (2011).
Yang, et al., Automatic Identification of Human Helminth Eggs on Microscopic Fecal Specimens Using Digital Image Processing and an Artificial Neural Network, IEEE Transaction on Biomedical Engineering 718 (IEEE 2001).
Geng, et al., Automated Worm Tracking and Classification, Conference Record of the Thirty-Seventh Asimolar Conference on Signals, Systems and Computers 2063 (2003).
Brunn, et al., Classification of Parasite Eggs Used as an Active Pharmaceutical Ingredient (API), Technical University of Denmark (2011).
Brunn, et al., Detection and Classification of Parasite Eggs for use in Helminthic Therapy, IEEE International Symposium on Biomedical Imaging 1627 (IEEE 2012).
Brunn, et al., Detection and Classification of Parasite Eggs for use in Helminthic Therapy, IEEE International Symposium on Biomedical Imaging (IEEE 2012).
Sommer, et al., Quantitative Characterization of Texture used for Identification of Eggs of Bovine Parasitic Nematodes, 72 Journal of Helminthology 179 (1998).
Nugent, et al., Using Active Learning to Annotate Microscope Images of Parasite Eggs, 26 Artificial Intelligence Review, 63 (Sep. 2007).
Peng, et al., Engineering Research on the Automatic Identification of Helminth Egg Images, 2 Journal of Hunan Normal University (Feb. 2005).
Zhao Yae, Automatic Recognition of Human Parasite Egg Pictures, 2 Chinese Journal of Stereology and Image Analysis 135 (Sep. 1997).
Daugschies, et al., Autofluorescence Microscopy for the Detection of Nematode Eggs and Protozoa, in Particular Isospora Suis, in Swine Faeces 87 Parasitology Research 409 (2001).

Image definitions

Orientation alignment

Shape profile computation

FIG. 8
Examples of the seven egg categories
Lateral singularized eggs
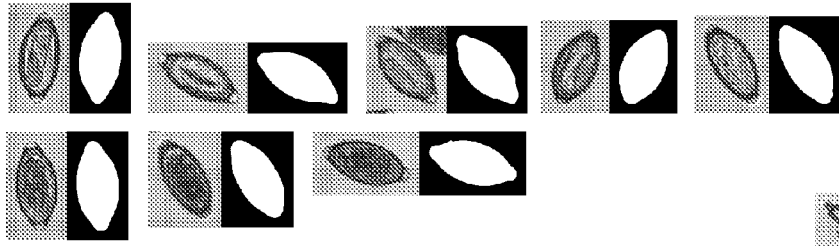
Upright singularized eggs
Lateral touching eggs
Upright touching eggs
Partly covered eggs
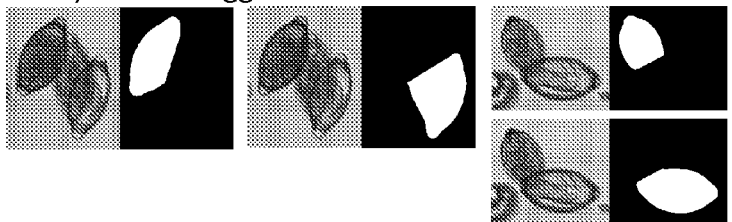
Multiple objects
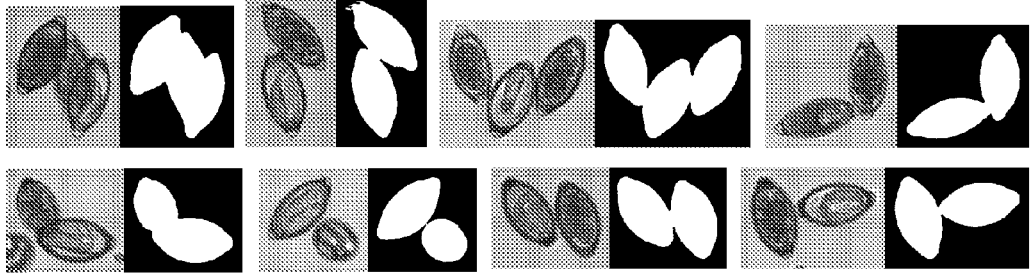
Foreign particles
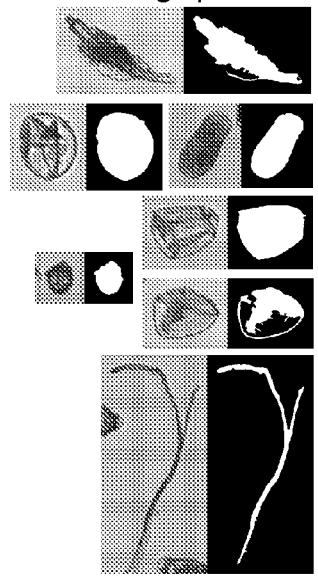

Spatial autocorrelation computation FIG. 10
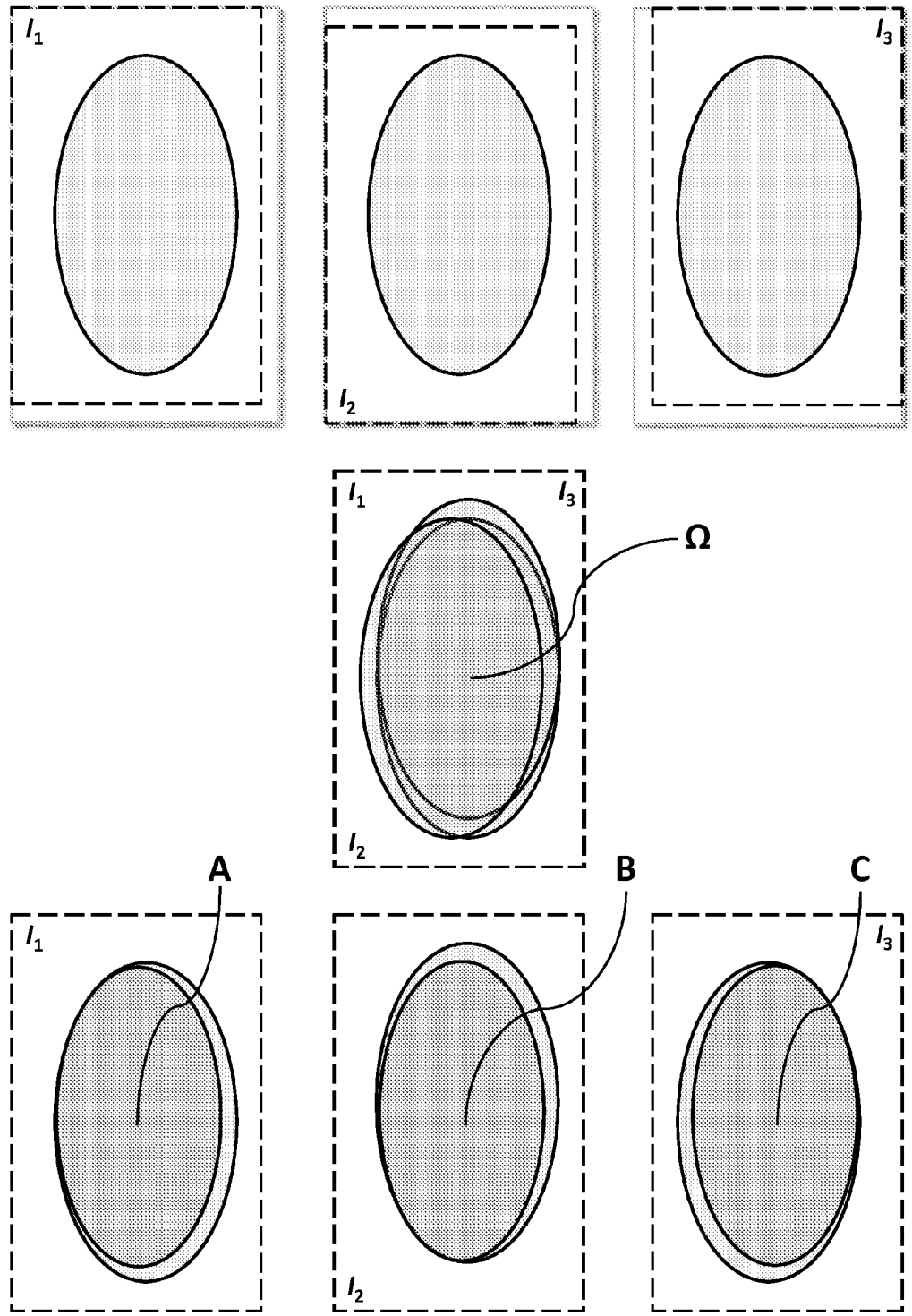

FIG. 11

Correlation formula

Let $I_1$ and $I_2$ be two monochromatic images of the same dimensions, and let $\Omega$ be a region inside $I_1$, i.e. a set of pixel coordinate pairs that are all within $I_1$. Let then $A$ be the subset of pixels in $I_1$ that are covered by $\Omega$, and let $B$ be the subset of pixels in $I_2$ that are covered by $\Omega$. Let furthermore $A(i,j)$ be the pixel intensity of $A$ at coordinate pair $(i,j)$, and similarly, let $B(i,j)$ be the pixel intensity of $B$ at coordinate pair $(i,j)$.

The correlation between $A$ and $B$ is then defined to be $$\mathrm{corr}_\Omega(A, B) = \frac{1}{|\Omega|} \sum_{(i,j) \in \Omega} \left( \frac{A_{(i,j)} - \mu_A}{\sigma_A} \cdot \frac{B_{(i,j)} - \mu_B}{\sigma_B} \right)$$

where $\mu_A$ is the mean of $A$ given by $$\mu_A = \frac{1}{|\Omega|} \sum_{(i,j) \in \Omega} A_{(i,j)}$$

and similarly for $\mu_B$, and $\sigma_A$ is the standard deviation of $A$ given by $$\sigma_A = \sqrt{\frac{1}{|\Omega|} \sum_{(i,j) \in \Omega} \left( A_{(i,j)} - \mu_A \right)^2}$$

and similarly for $\sigma_B$. $|\Omega|$ denotes the number of pixel coordinate pairs in region $\Omega$.

FIG. 12

Edge orientations

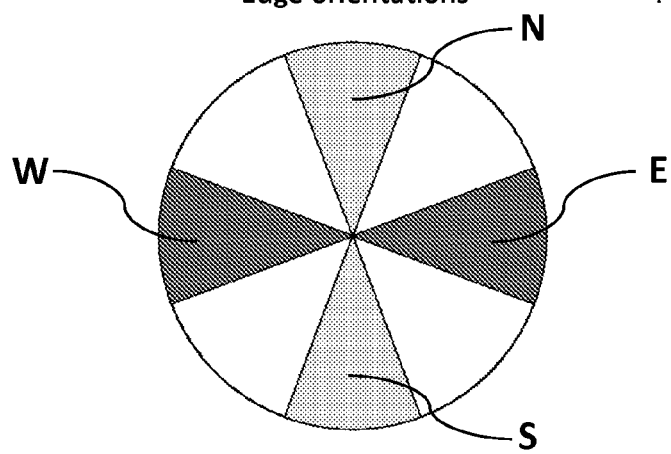

Definition of edge orientations. Each interval is 45 degrees wide. N and S constitute the longitudinal edge count while W and E constitute the transverse edge count in the edge direction quantification.

Classification graphs I  FIG. 13
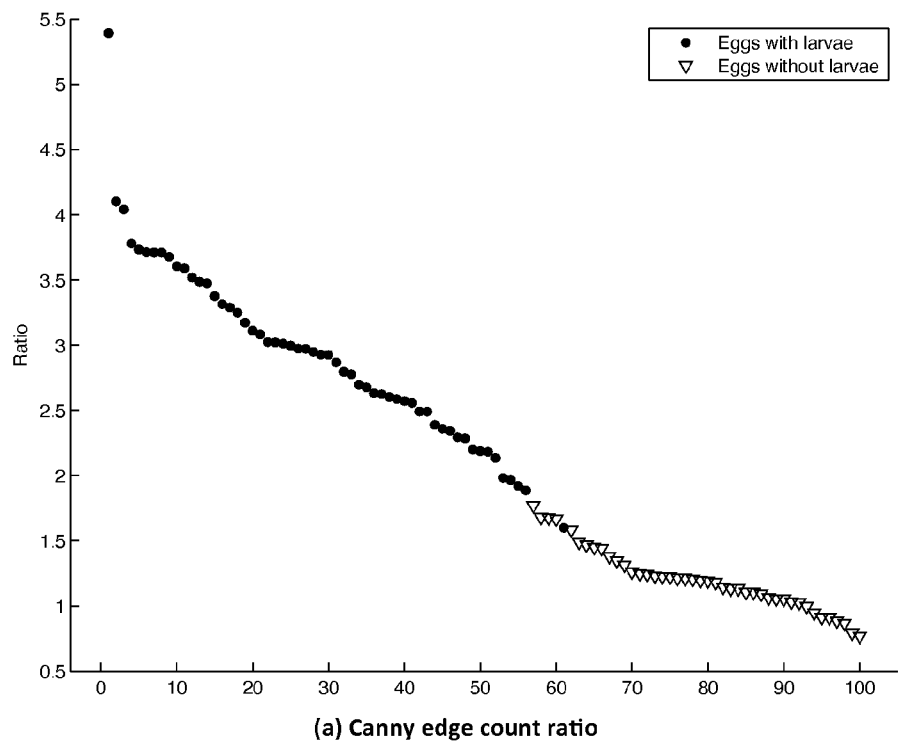
(a) Canny edge count ratio
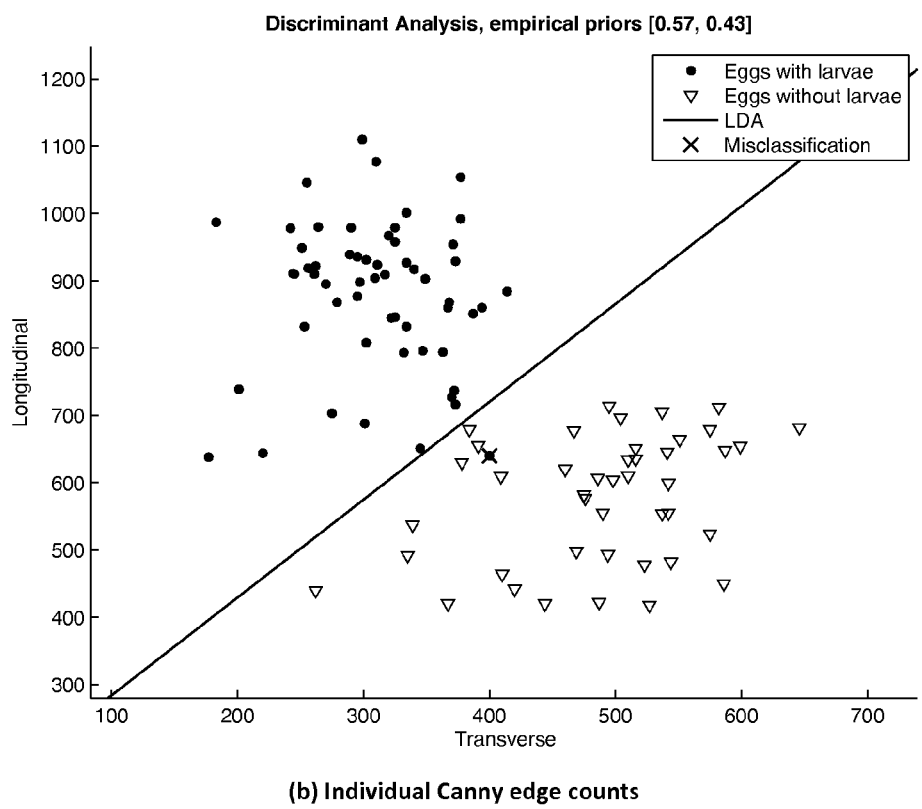
(b) Individual Canny edge counts FIG. 14
Classification graphs II
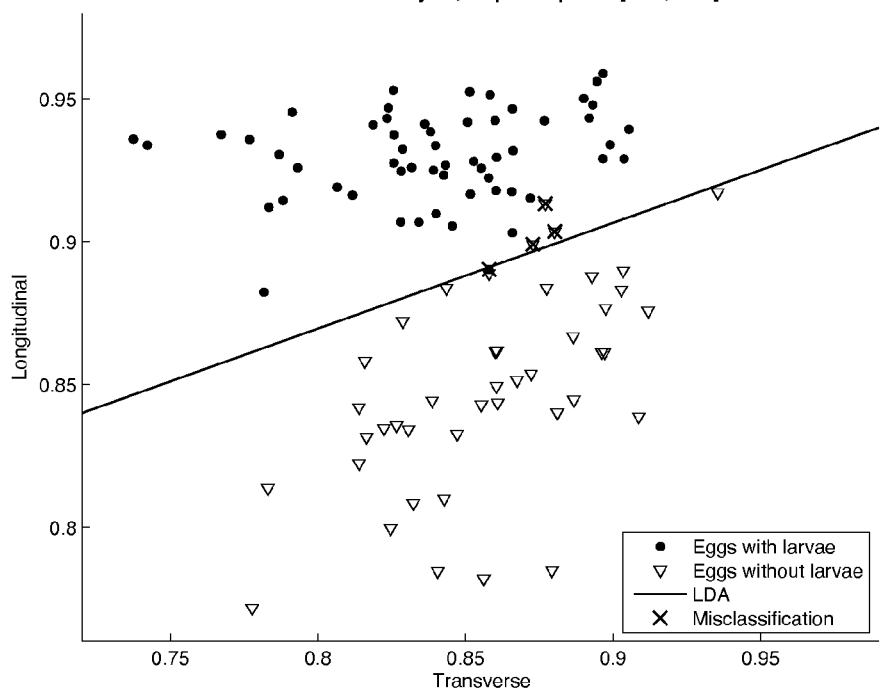
(a) Longitudinal and transverse autocorrelation
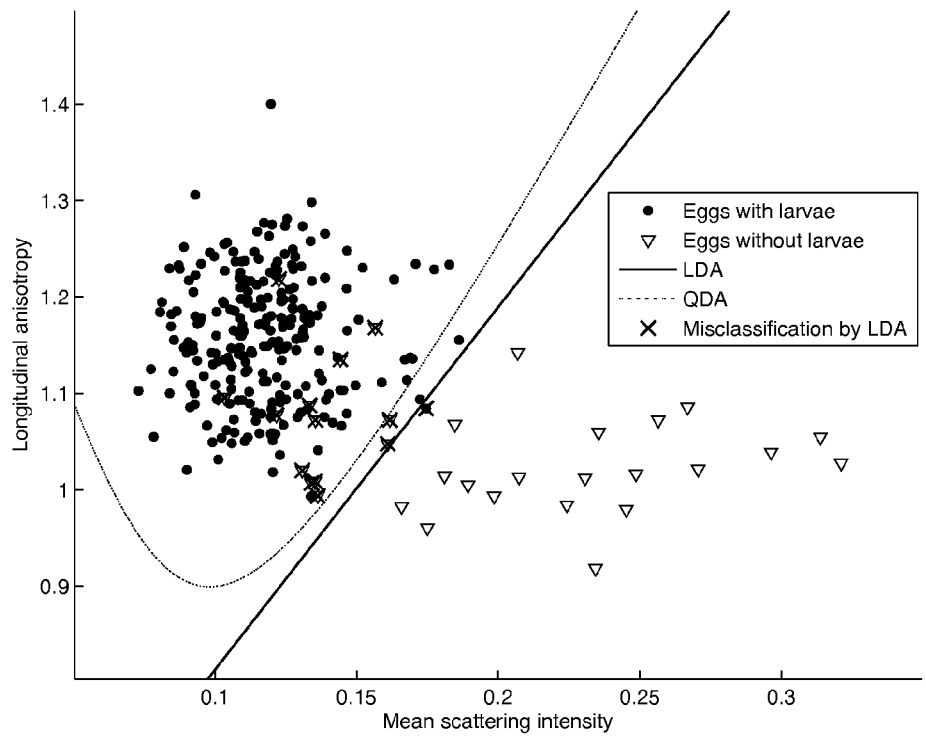
(b) Longitudinal anisotropy and Mean scattering intensity

Developmental stages  FIG. 15
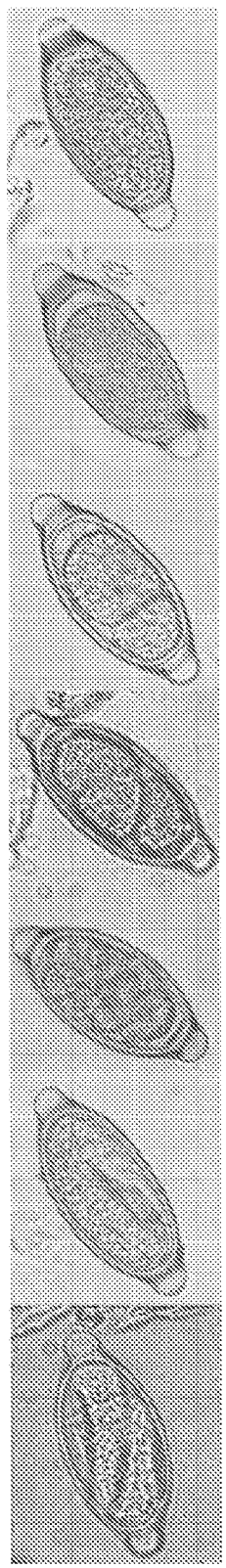
Unsegmented egg
1 cell
1st clevage (2 cells)
2nd clevage (3 cells)
Subsequent clevages (several cells)
Early larva (short, thick, cylindrical embryo)
Fully developed larva (long, slender, coiled)

Examples of corresponding brightfield and darkfield images   FIG. 16
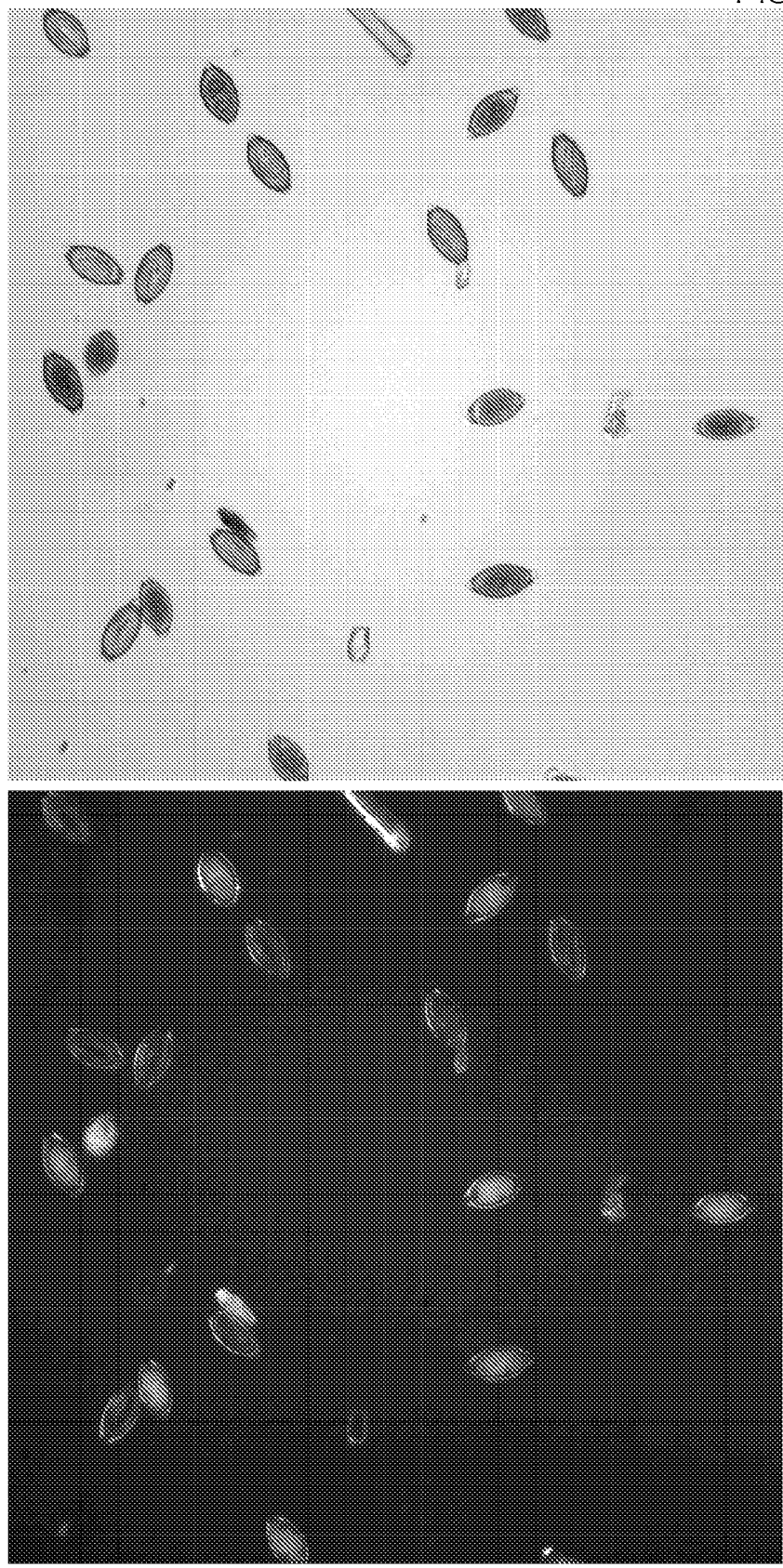

COMPUTER VISION BASED METHOD FOR EXTRACTING FEATURES RELATING TO THE DEVELOPMENTAL STAGES OF *TRICHURIS* SPP. EGGS

This application claims priority to U.S. Provisional application 61/639,229 filed Apr. 27, 2012.

FIELD OF THE INVENTIONS

The present invention relates to a computer vision based method for extracting features relating to the developmental stages of *Trichuris* spp. eggs, wherein for the final developmental stages a larva is present inside the egg. More particularly, the method may be used for extracting features for *Trichuris suis* eggs.

BACKGROUND OF THE INVENTIONS

Purpose of the Invention

Exposure to helminths (intestinal worms) such as whipworms have been shown to have a mitigating effect on a number of autoimmune diseases such as Crohn's disease and Ulcerative colitis. This new treatment is known as helminthic therapy and it utilizes the immunoregulatory behavior of helminths in the intestines where orally administered whipworm eggs hatch into larvae which establish for a shorter period of time in a self-limiting intestinal infection.

Only eggs that contain a fully developed larva can induce the positive immune response. Thus, assessment of the medicinal potency is correlated to the proportion of eggs with fully developed larvae in a given egg suspension. The presented invention enables an automated, non-invasive and cost-effective way of assessing the biological potency of a particular egg suspension.

Related Work

Several research papers have studied the use of image analysis to separate parasite eggs of distinct species, including helminths. Yang et al. and others had some success in separating different species of human helminth eggs based on their exterior size and shape. Such approach cannot be used for developmental stages and thereby biological potency since there are no visible differences in the exterior size and shape of eggs that contain a larva and eggs that do not. Similarly, the larvae in the egg may not be fully developed (see FIG. 15) and thereby without the ability to establish in the intestine.

SUMMARY

According to the present invention there is provided a computer vision based method for extracting features relating to the developmental stages of *Trichuris* spp. eggs, wherein for the final developmental stages a larva is present inside the egg, said *Trichuris* spp. eggs having a substantially oblong or elliptical shape with a protruding polar plug at each end, the shape of the *Trichuris* spp. eggs thereby defining a longitudinal direction and a transverse direction of the eggs, said method comprising:
a) obtaining and storing one or more digital images of *Trichuris* spp. eggs suspended in a liquid solution,
b) detecting one or more *Trichuris* spp. eggs in the image(s), and
c) extracting one or more features from an egg content image region representing at least part of the egg contents of a detected egg.

Thus, the extracted features are related to the contents of an egg, and may also be denoted egg-content-features.

According to one or more embodiments of the invention, the *Trichuris* spp. eggs are *Trichuris suis* eggs.

It is preferred that for step a) the stored digital images of the *Trichuris* spp. eggs comprises one or more bright-field images, and that for step c) one or more features are extracted from an egg content image region being a bright-field egg content image region.

It is also preferred that one or more features are extracted from an egg content image region being extracted from an image or image region which includes a full representation of a detected *Trichuris* spp. egg. The bright-field egg content image region may also be extracted from a bright-field image or image region, which includes a full representation of a detected *Trichuris* spp. egg In a preferred embodiment the extracted egg content image region excludes the polar plugs of the detected *Trichuris* spp. egg. It is also preferred that the extracted egg content image region excludes the shell of the detected *Trichuris* spp. egg. Here, the extracted egg content image region may have a substantially elliptical shape, thereby defining a content ellipse image.

It is preferred that the extraction of one or more features from the egg content image region includes one or more measurements of the direction-dependent structures of the egg contents. Here, the extraction of one or more features from the egg content region may include one or more measurements of the longitudinal structures of the egg contents and/or one or more measurements of the transverse structures of the egg contents. One or more measurements of the longitudinal structures may be based on a measure of the linear structures and/or edge structures in the longitudinal direction, and one or more measurements of the transverse structures may be based on a measure of the linear structures and/or edge structures in the transverse direction.

According to an embodiment of the invention the linear structures and/or edge structures are measured at a predetermined scale.

According to another embodiment of the invention one or more measurements of the longitudinal structures may be based on a measure of the linear structures and/or edge structures in the longitudinal direction at one or more scales in a multi-scale representation of the image region from which the features are extracted. Also one or more measurements of the transverse structures may be based on a measure of the linear structures and/or edge structures in the transverse direction at one or more scales in a multi-scale representation of the image region from which the features are extracted. The multi-scale representation of the image region from which the features are extracted may be a pyramid representation or a scale space representation.

It is within one or more embodiments of the invention that one or more measurements of the longitudinal structures of the egg contents is based on a longitudinal comparison of pixels intensities obtained from similarly addressed pixels in first and second image parts representing at least part of the egg contents of a detected egg, with the second image part being obtained by shifting the first image part one or more pixels in a direction substantially following the longitudinal direction of the egg. It is also within one or more embodiments of the invention that one or more measurements of the transverse structures of the egg contents is based on a transverse comparison of pixel intensities obtained from similarly addressed pixels in the first image part and a third image part representing at least part of the egg contents of a detected egg, with the third image part being obtained by shifting the first image part one or more pixels in a direction substantially following the transverse direction of the egg.

It is preferred that the longitudinal comparison of pixel intensities from the first and second image parts comprises calculating a longitudinal correlation coefficient $\rho_{long}$ for pixel intensities representing at least part of the similarly addressed pixels, and that the transverse comparison of pixel intensities from the first and third image parts comprises calculating a transverse correlation coefficient $\rho_{trans}$ for pixel intensities representing at least part of the similarly addressed pixels. Here, the feature extraction may further include a ratio measure based on the ratio between the longitudinal correlation coefficient $\rho_{long}$ and the transverse correlation coefficient $\rho_{trans}$.

For embodiments of the invention wherein one or more measurements of the longitudinal structures are based on a measure of the edge structures in the longitudinal direction, and one or more measurements of the transverse structures are based on a measure of the edge structures in the transverse direction, then it is preferred that expressions representing a measure or measures of the edge structures in the longitudinal and transverse directions are obtained by use of an edge detector algorithm. Here, the edge detector algorithm may be selected from the following algorithms: the Canny edge detector algorithm, the Sobel edge detector algorithm, and the Prewitt edge detector algorithm.

The expression or expressions representing the edge structures in the longitudinal direction, longitudinal edge count, may be defined as the number of edge pixels of the egg contents, which is given by the edge detector algorithm, and which are oriented substantially in the longitudinal direction, and the expression or expressions representing the edge structures in the transverse direction, transverse edge count, may be defined as the number of edge pixels of the egg contents, which is given by the edge detector algorithm, and which is oriented substantially in the transverse direction. The longitudinal edge count may be defined as the number of edge pixels of the egg contents, which is given by the edge detector algorithm and which are oriented in the longitudinal direction plus/minus an angle within the range of 10-45 degrees, such as within the range of 15-35 degrees, such about 22.5 degrees, and wherein the transverse edge count is defined as the number of edge pixels of the egg contents given by the edge detector algorithm and being oriented in the transverse direction plus/minus an angle within the range of 10-45 degrees, such as within the range of 15-35 degrees, such as about 22.5 degrees.

The present invention also covers embodiments, wherein in step a) the stored digital images of the *Trichuris* spp. eggs comprises one or more dark-field images and wherein in step c) one or more features are extracted from an egg content image region being a dark-field egg content image region. Here, one or more features may be extracted from a dark-field egg content image region being extracted from a dark-field image region which includes a full representation of a detected *Trichuris* spp. egg. Preferably, the extracted dark-field egg content image region excludes the polar plugs of the detected *Trichuris* spp. egg. It is also preferred that the extracted dark-field egg content image region excludes the shell of the detected *Trichuris* spp. egg, and here the extracted dark-field egg content image region may have a substantially elliptical shape, thereby defining a content ellipse image.

According to one or more embodiments of the invention the feature extraction of step c) may include dark-field features extracted from the dark-field egg content image region, where the dark-field feature extraction is based on variations in pixel intensities measured or extracted for at least part of the dark-field egg content image region. The dark-field feature extraction may comprise a computation of the average of the extracted pixel intensities. According to embodiments of the invention the dark-field feature extraction may comprise a computation of the mean of the extracted pixel intensities, mean scattering intensity, and/or a computation of the median of the extracted pixel intensities, median scattering intensity.

The present invention also covers embodiments, which further comprises a classification step, wherein at least part of the features extracted from an egg content image region representing a detected egg are used for classifying the detected egg. Here, the classification of the detected egg may be a binary classification with respect to the developmental stage of egg, and the detected egg may be classified as either containing a larva or not containing a larva.

The classification of the detected egg may also be a multi-class classification with respect to the developmental stage of egg, where the multi-class classification comprises at least three classes of developmental stages.

The classification may be at least partly based on extracted features, for which features the extraction includes one or more measurements representing longitudinal structures and transverse structures of the egg contents. Here, the classification may be at least partly based on a ratio measure obtained from a measure representing the longitudinal structures of the egg contents and a measure representing the transverse structures of the egg contents. It is preferred that the one or more measurements representing the longitudinal structures are based on a measure of the linear structures and/or edge structures in the longitudinal direction, and that the one or more measurements representing the transverse structures are based on a measure of the linear structures and/or edge structures in the transverse direction. The measurements of the linear structures and/or edge structures in the longitudinal and transverse directions may be measured according to one or more of the herein mentioned embodiments. It is within an embodiment of the invention that a measure representing the longitudinal structures of the egg contents have to exceed a corresponding measure representing the transverse structures of the egg contents by a predetermined factor being larger than one in order to have the egg classified as containing a larvae.

The present invention also covers embodiments, wherein the classification is at least partly based on extracted dark-field features, where the dark-field features may be extracted according to one or more of the embodiments described herein.

BRIEF DESCRIPTION OF THE DRAWINGS

List of figures:
FIG. 8: Examples of the seven egg categories
FIG. 10: Spatial autocorrelation computation
FIG. 11: Correlation formula
FIG. 12: Edge orientations
FIG. 13: Classification graphs I
FIG. 14: Classification graphs II
FIG. 15: Developmental stages
FIG. 16: Examples of corresponding brightfield and dark-field images Egg Characteristics The presented analysis relates to *Trichuris* spp. eggs, i.e. eggs from various species of the genus *Trichuris*, also known as whipworms. *Trichuris* spp. eggs, in the following denoted *Trichuris* eggs, have a distinct, lemon-like shape and a smooth outer shell. The shape can be described as a prolate spheroid, also known as a prolate ellipsoid of revolution, with protruding, operculate plugs in each end (apex). When observed from the side (lateral view), the shape of a i egg is oblong and elliptical with protruding plugs at the ends.

The average length (major axis) and width (the two minor axes) of *Trichuris* eggs depend to a certain degree on the specific species. The sizes of some of the main species of *Trichuris* are:

*Trichuris trichiura* (human whipworm): 50-58×22-27 µm, 50-54×22-23 µm.

*Trichuris suis* (pig whipworm): 50-68×21-31 µm, 60×25 µm

*Trichuris muris* (mouse whipworm): 67-70×31-34 µm

*Trichuris vulpis* (canine whipworm): 70-90×32-41 µm

*Trichuris ovis* (ruminant whipworm): 70-80×30-42 µm

Experimental Setup

A generic setup is as follows:

A 40 µl sample of an egg suspension with approximately 40.000 eggs per ml is placed on a microscope slide or a similar container with a cover glass on top.

The slide is placed under an upright or inverted microscope and images are acquired at around 100-200× magnification, in both brightfield and darkfield illumination. Examples of corresponding brightfield and darkfield images can be seen in FIG. 16.

DEFINITIONS

The following section defines some of the terms that are used throughout the description. It includes terms related to egg positions and egg categorization as well as image handling and digital image analysis.

Lateral

A lateral object is a prolate object that is placed on its side.

A lateral egg is an egg lying on its side. In an image, the outline of such an egg is elliptical with protruding polar plugs at the ends.

Upright

An upright object is a prolate object that is placed on one of its apices.

An upright egg is an egg that is standing upright on one of its polar plugs. In an image, the outline of such an egg is circular or close to circular with a diameter corresponding to the width of a lateral egg.

Singularized

A singularized object is an object that does not touch or overlap with other objects, i.e. is clearly separated from nearby objects.

A singularized egg is an egg that does not touch or overlap with other eggs or foreign particles.

Touching

A touching object is an object that touches, but does not overlap with, other objects.

A touching egg is an egg that touches one or more other eggs or impurities, but is not overlapping with them, i.e. its entire content region is clearly visible.

Partly Covered Egg

A partly covered egg is an egg whose full outline is not distinguishable because the egg is covering or covered by one or more other objects, for instance other eggs.

Foreign Particle/Impurity

The terms 'foreign particle' and 'impurity' are used interchangeably to describe all objects in the images that are not *Trichuris* eggs. This includes both organic and inorganic impurities such as dust particles, fibers, minerals, plant remnants, and pollen, as well as gas, air, or oil bubbles and non-*Trichuris* eggs.

Multiple Objects

The term 'multiple objects' is used to describe two or more objects that touch or overlap. In the analysis these are seen and treated as the same object until they are split into a number of separate objects.

ROI, Blob, Subimage

Figure 5:
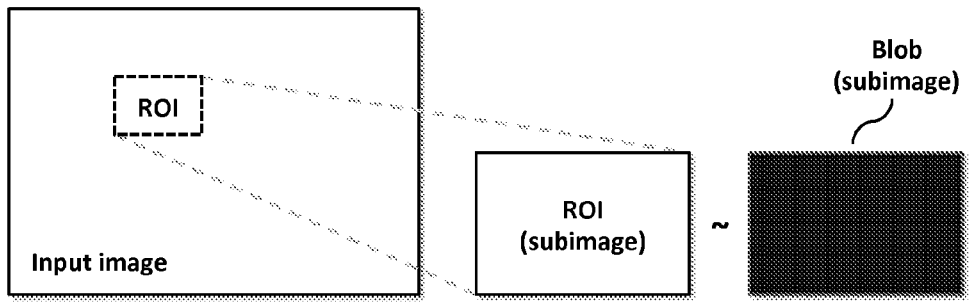
FIG. 5: Image definitions

A ROI (region-of-interest) is a rectangular, cropped region of an input image that contains the object of interest plus a margin of its surroundings. The blob (binary large object) is a binary image of the same dimensions that indicates what pixels that belong to the object of interest in the ROI image. In this description, these are collectively called 'subimages' to distinguish them from the input images of the overall system. These terms are illustrated in FIG. 5.

Egg Orientation/Egg Direction

Figure 6:
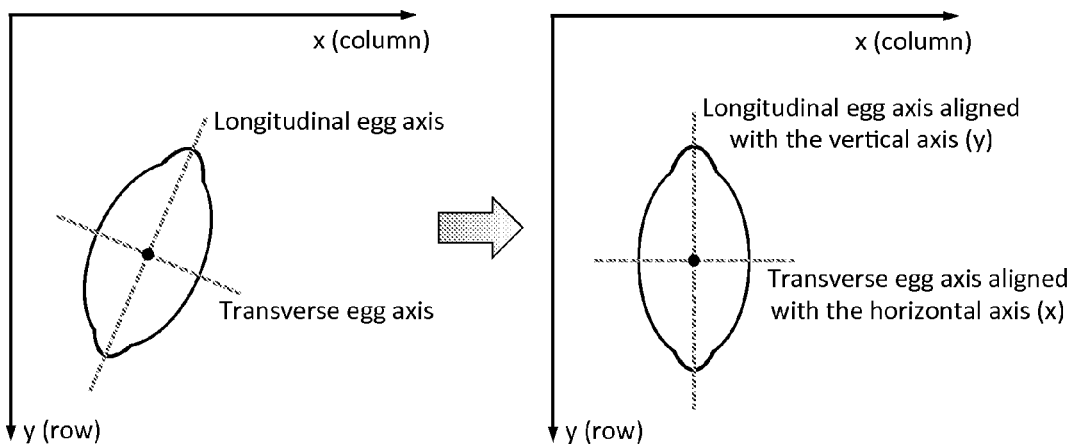
FIG. 6: Orientation alignment
Figure 7:
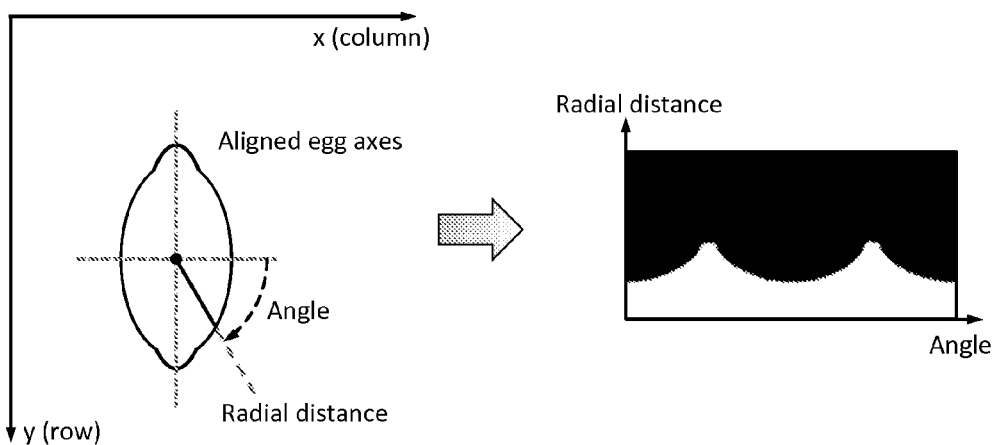
FIG. 7: Shape profile computation

The orientation of an egg is the angle between its longitudinal axis and the image x-axis. It is also called the direction of the egg. See left half of FIG. 6 for an illustration of the image coordinate system and the egg axes.

Developmental Stages/'Containing a Larva'

The level of embryonation and larval development inside *Trichuris* spp. eggs, here referenced for *Trichuris suis* eggs, can be assessed by following morphological changes inside the egg shell. The eggs can be classified as either unsegmented eggs, eggs undergoing cellular division (1, 2, 3, 6, and many blastomeres), eggs containing cylindrical embryo, and eggs with fully developed, defined infective L1 larva. The term 'containing a larva' is used to describe the latter two of these. The developmental stages are illustrated in FIG. 15.

DETAILED DESCRIPTION OF THE INVENTIONS

The description of the presented invention is built around four main flowcharts that can be seen on FIGS. 1 through 4. These are described one at a time in the following, and additional figures are introduced along the way when needed.

Figure 1:
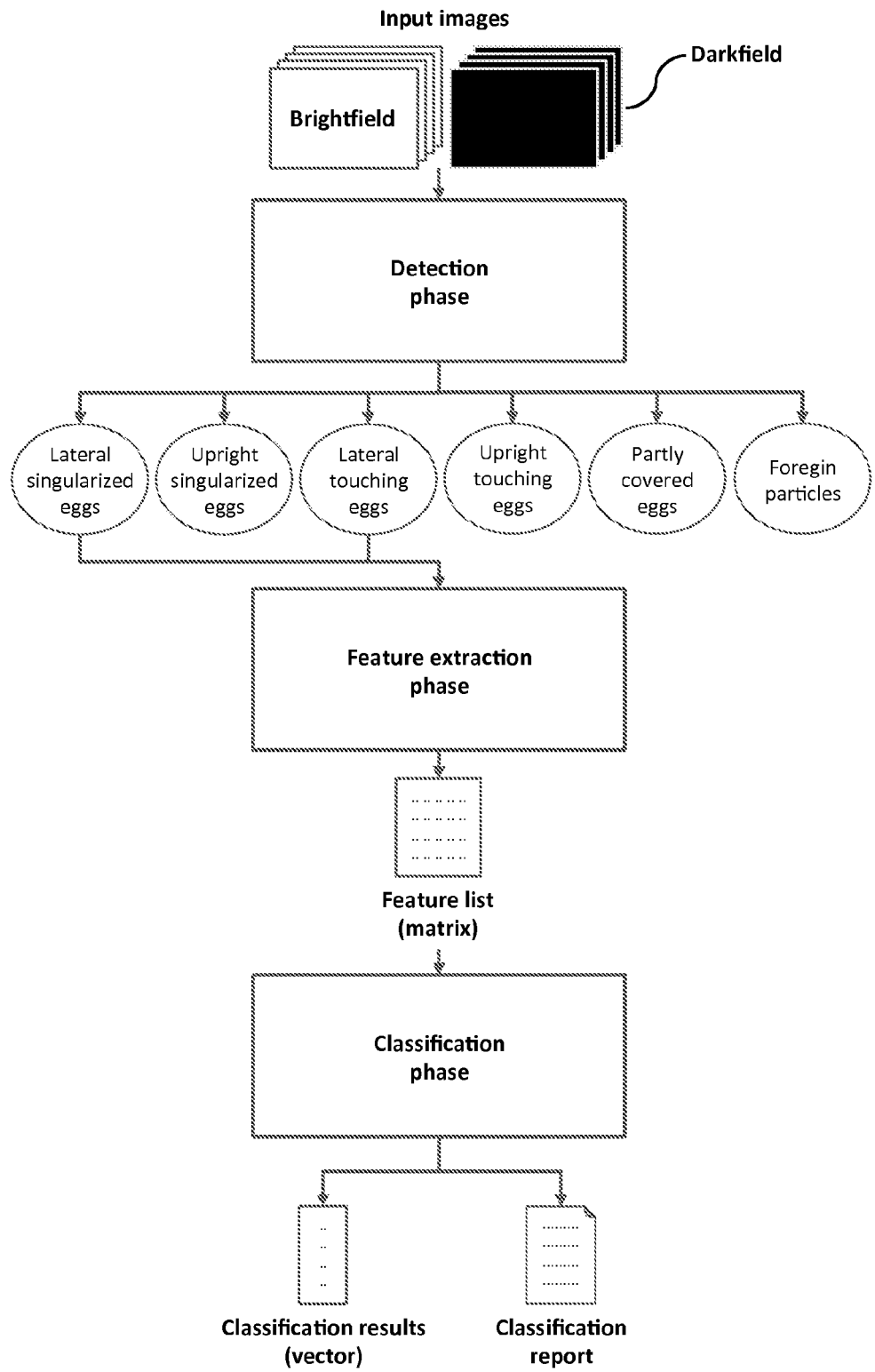
FIG. 1: Complete egg analysis system

FIG. 1: Complete Egg Analysis System

Figure 2:
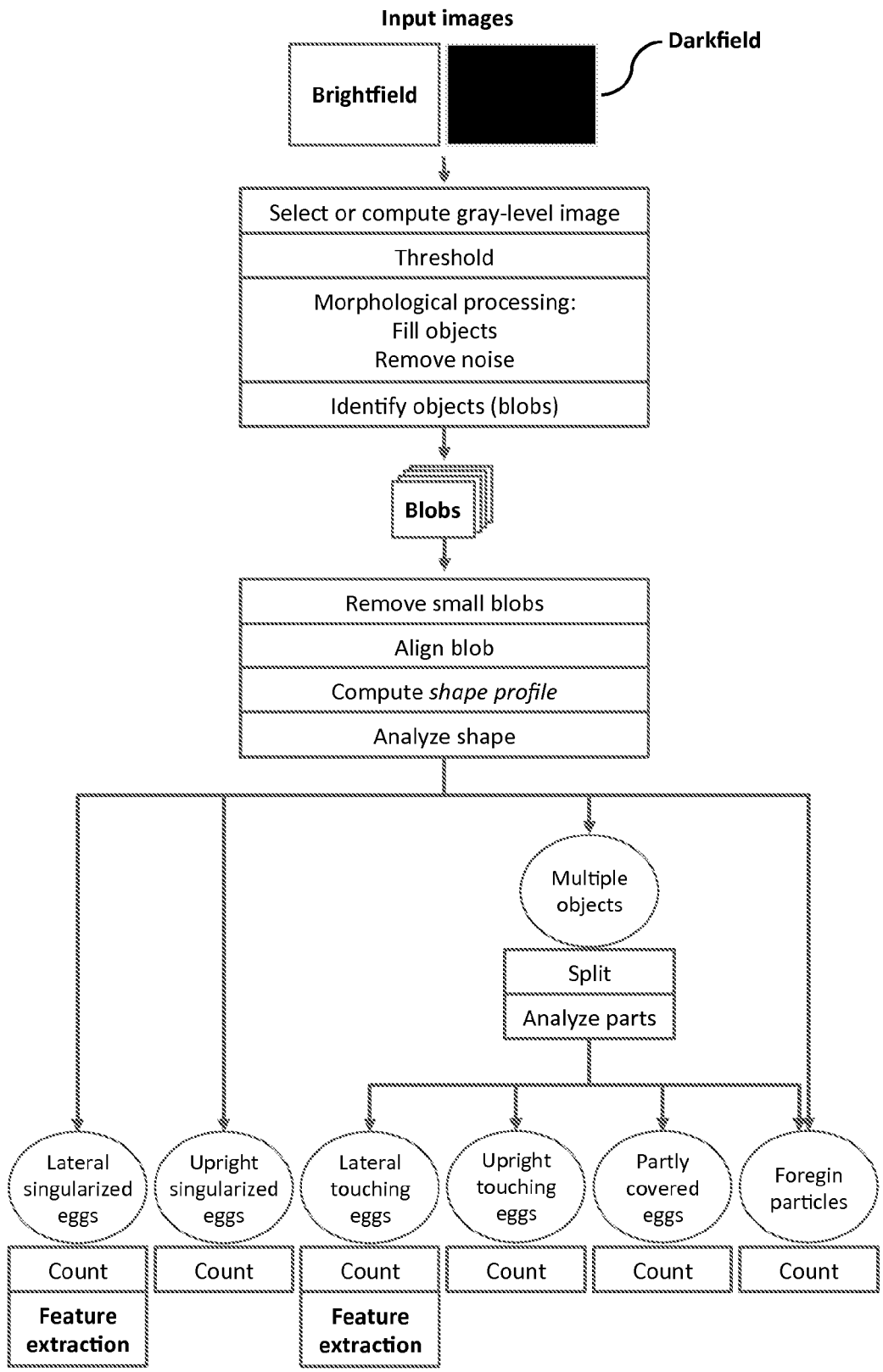
FIG. 2: Detection phase

One or more microscopic images are passed to the Detection phase (see FIG. 2). The microscopic images can be both multispectral (more than one wavelength) and multimodal (more than one illumination mode). An image can therefore consist of several bands, each representing a combination of a wavelength (for instance ultraviolet, a visible color, or near-infrared) and an illumination mode (for instance brightfield, darkfield, or phase contrast).

In the Detection phase, all foreground objects in a chosen or computed band of each input image are detected and assigned one of the following six categories:

Lateral singularized eggs—*Trichuris* eggs that do not touch or overlap with other objects and lie down on their side.

Upright singularized eggs—*Trichuris* eggs that do not touch or overlap with other objects and stand upright on one of their plugs.

Lateral touching eggs—Lateral *Trichuris* eggs that are touching but not covering or covered by other objects.

Upright touching eggs—Upright *Trichuris* eggs that are touching but not covering or covered by other objects.

Partly covered eggs—*Trichuris* eggs whose full outline is not distinguishable since the egg is covering or covered by other objects, for instance other eggs.

Foreign particles—All objects in the images that are not *Trichuris* eggs.

During the Detection phase an object can be assigned an additional, intermediate category:

Multiple objects—Two or more objects that touch or overlap. In the analysis these are seen and treated as the same object until they are split into a number of separate objects.

See also the definitions of the terms used in the category names in the Definitions section above. In the following description, the term 'eggs' is referring to '*Trichuris* eggs' unless otherwise noted.

Examples of ROI and blob subimages of each category can be seen on FIG. 8.

All of the objects in the six main categories are counted. The total number of detected eggs (categories 1 through 5) can be used to assess the concentration of the analyzed egg suspension, i.e. the number of eggs per ml. For a good assessment, the analyzed sample should be representative of the entire suspension.

The particle count (category 6) can be used to assess the purity of the analyzed egg suspension, for instance measured as the number of impurities or foreign particles per ml. Further analysis of the impurities, for instance a multiclass classification of the detected particles, is not presented here.

Only the Lateral singularized eggs and the Lateral touching eggs are passed to the Feature Extraction phase (FIG. 3) since these have clearly visible and unobstructed contents. Here, relevant quantitative features of the egg contents are extracted for each egg. The resulting list of features is used in the Classification phase (FIG. 4), where each of the eggs is classified as either containing a larva or not (binary classification), or by their developmental stage (multiclass classification). The classification results can be used as an indicator of the biological potency of the egg suspension.

The system finally produces a report of the analysis results, including detection results (e.g. listings and subimages of the detected objects and their categories), feature extraction results (e.g. feature lists), and classification results (e.g. assigned classes, certainty measures of the assigned classes etc.).

FIG. 2: Detection Phase

This description and FIG. 2 illustrate one possible way of detecting the *Trichuris* eggs in an input image.

(1) Select or Compute Gray-Level Image

The detection of the eggs is done on a single gray-level (monochromatic) image. This gray-level image can be one of the following:

A band from the original image (corresponding to one wavelength or one channel of RGB)

A linear combination of bands, e.g. a standard grayscale representation or a band from the output of a dimensionality reduction algorithm like principal component analysis (PCA) or canonical discriminant analysis (CDA).

A non-linear combination of bands, e.g. a channel from another color space, for instance the V-channel of HSV, or a band from the output of a nonlinear dimensionality reduction algorithm.

(2) Threshold

The gray-level image is thresholded resulting in a binary image indicating all foreground pixels, in this case pixels with values below the threshold. The thresholding can be either fixed (for instance at 0.6), automatic (for instance using Otsu's method), or adaptive to local regions of the image.

(3) Morphological Processing

The morphological processing used to prepare the binary image for object detection is hole filling and morphological closing.

(4) Identify Objects (Blobs)

Blobs (binary large objects)—connected groups of foreground pixels—are extracted using a connected-components labeling.

(5) Remove Small Blobs

Small blobs are removed if their area (pixel count) is under a predefined threshold (e.g. 1000 pixels). Each of the remaining blobs are then processed one at a time.

(6) Align Blob

A copy of the blob and the corresponding original gray-level image are created. These are then aligned with the image axes as illustrated on FIG. 6, by being rotated the same number of degrees so that the longitudinal direction of the object is aligned with the vertical axis of the image coordinate system.

(7) Compute Shape Profile

The radial distance from the blob's centroid (center of mass) to the edge of the blob at angles from 0 to 360 degrees is computed. The resulting set of (angle,distance)-measurements are denoted the 'shape profile' of the blob. A similar approach is used in.

(8) Analyze Shape

The blob and its shape profile are then analyzed in order to assign a category to the blob. The analysis consists of the following steps:

1) Compare the shape profile against a model shape profile of an 'ideal' lateral singularized egg. Assign it the category "Lateral singularized egg" if these are sufficiently similar. The similarity measure could for instance be the sum of absolute differences between the two shape profiles, which would then be compared to a threshold value in order to make the decision.

2) Compare shape profile against a model shape profile of an 'ideal' upright singularized egg. Similarly to the above, assign it the category "Upright singularized egg" if these are sufficiently similar.

3) Compute the 'solidity' of the blob as the ratio between the area of the blob and the area of the blob's convex hull. Blobs with a low solidity and an area somewhat larger (for instance 1.2 times larger) than the area of an 'ideal' lateral singularized egg are given the intermediate category of "Multiple objects", the rest are assigned the category "Foreign particle".

4) If given the category "Multiple objects", the blob is split into one or more smaller blobs using a clump splitting algorithm, e.g. using concavity analysis or template matching. Each of these new blobs is then categorized as either "Lateral touching egg" or "Upright touching egg" if the objects did not overlap, "Partly covered egg" if it did overlap with another object but still can be identified as an egg, or "Foreign particle" if none of the above.

Figure 3:
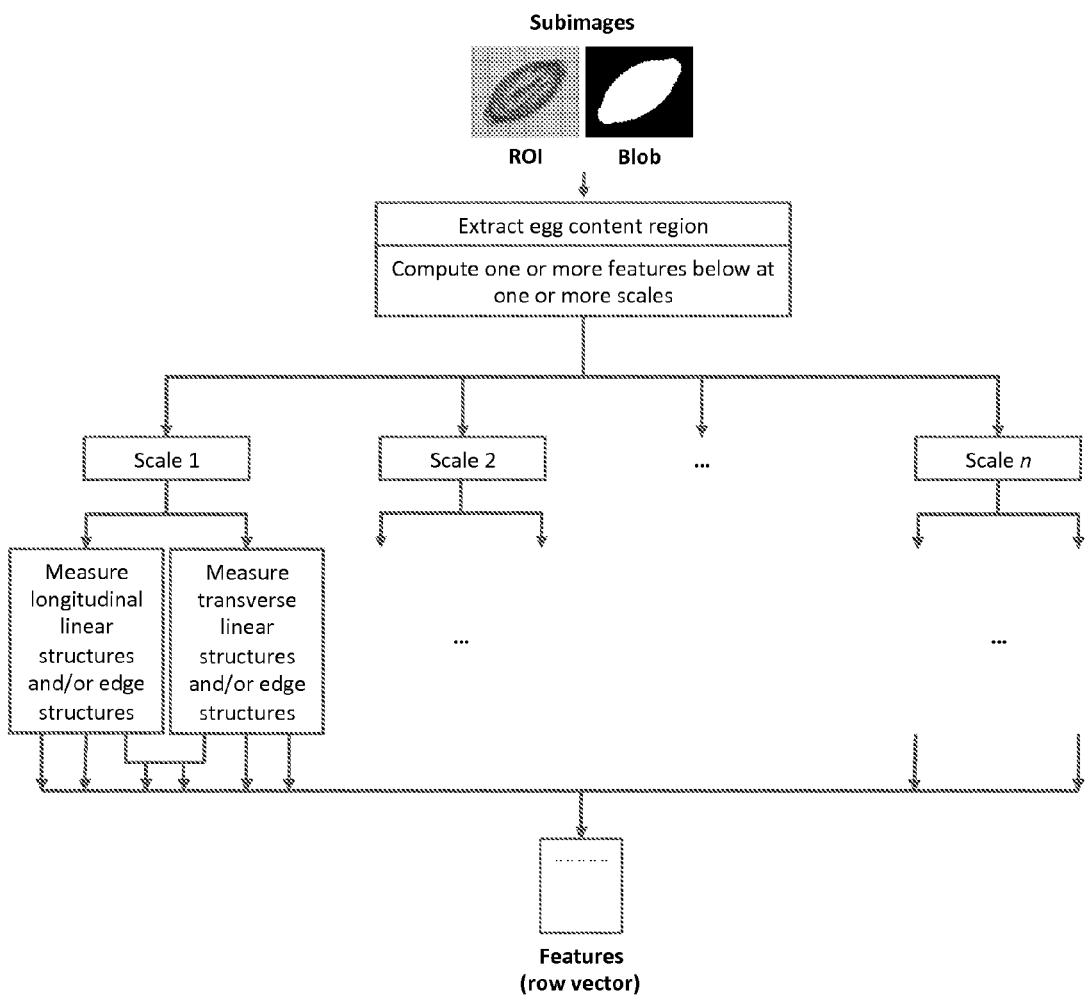
FIG. 3: Feature extraction phase

FIG. 3: Feature Extraction Phase

The input to the feature extraction phase consists of at least two images, a ROI subimage and a blob subimage. Additionally it may include any number of other ROI subimages of the same region from other bands or illumination modes, like a darkfield ROI subimage used for darkfield-based features.

(1) Extract Egg Content Region

Figure 9:
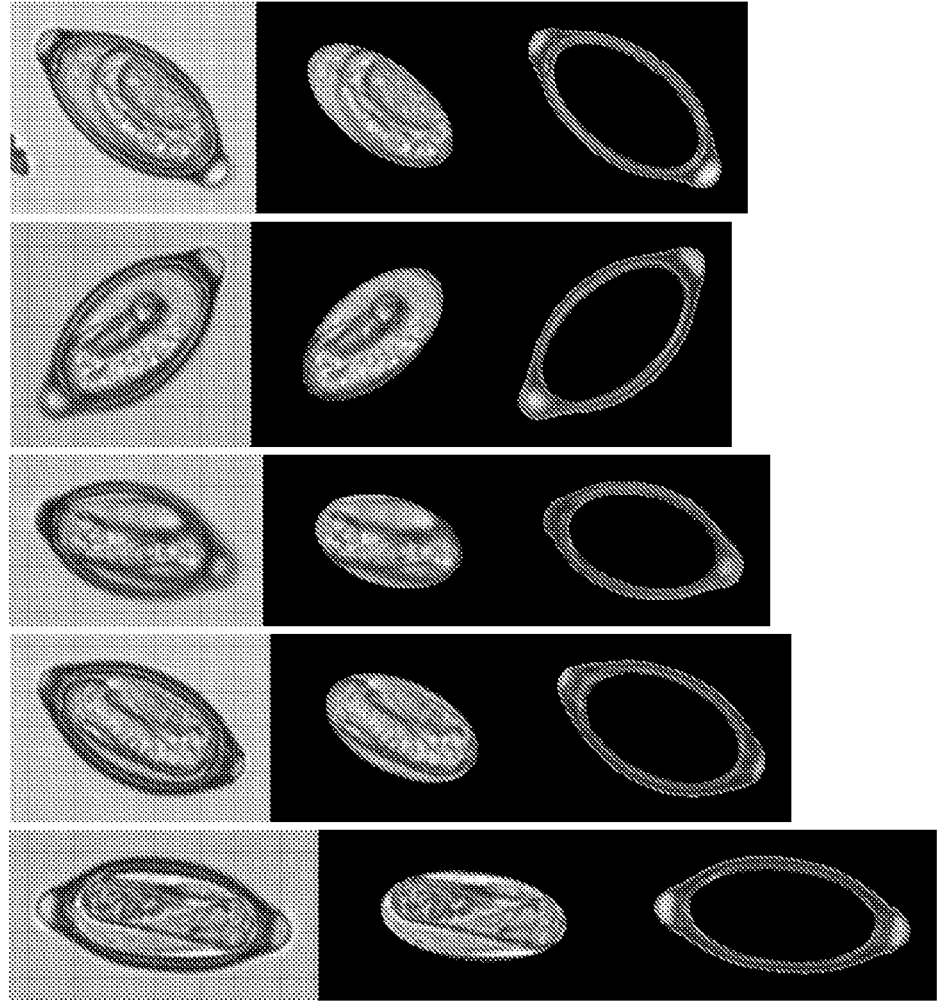
FIG. 9: Egg content region extraction

The 'egg content region', i.e. the region inside the egg where the egg contents are located, is extracted for further analysis. One way to do this, which is independent of the egg orientation, is illustrated in FIG. 9 and consists of the following:

1) Compute the ellipse that has the same normalized second central moments as the blob. This is denoted the 'blob ellipse'. See FIG. 9(*c*).

2) Define a new ellipse with minor axis of the same length and major axis of 95% of the length of the blob ellipse as well as the same orientation as the blob ellipse. This ellipse is denoted the 'body ellipse' since it indicates the body of the egg including egg shell but without the polar plugs. See FIG. 9(d) and (e).

3) Define a new ellipse with axis lengths at 80% of the length of the corresponding body ellipse axis. This ellipse is denoted the 'content ellipse' since it indicates the contents of the egg. See FIG. 9(f). The image region covered by this ellipse is used as the 'egg content region' in the subsequent analysis.

Examples of egg content regions extracted this way can be seen on FIG. 9(g).

(2) Compute One or More Features Below at One or More Scales

One or more features are computed for each egg based on the extracted egg content region. Each feature is computed at a chosen scale that depends on the size of the details and structures that the feature is meant to measure. Besides choosing the scale directly and resizing the image to this scale, there are several ways to represent and work with images at multiple scales; three important ways being scale space representation, image pyramid representation, and multi-resolution analysis.

(3) Measure Longitudinal/Transverse Linear Structures and/or Edge Structures

When a scale has been selected, the direction-dependent linear structures and/or edge structures of the egg contents are measured at this scale. The measurements are carried out according to the longitudinal and transverse directions of the egg, either by measuring them in-place at the eggs original orientation or by aligning the egg with the horizontal and vertical image axes via rotation, as illustrated on FIG. 6.

Below are presented a range of examples of methods for constructing features based on measurements of the longitudinal and transverse structures of the egg contents. The idea behind this is to construct features based on the measurements of the direction-dependent structures and use them in the classification phase. The underlying hypothesis is that eggs containing visible larvae have more prominent longitudinal structures than transverse structures due to the way larvae are positioned inside the eggs if present. Fully developed larvae have more than partly developed larvae (see FIG. 15).

The measurement of longitudinal and transverse structures can sometimes be simplified by aligning the longitudinal and transverse axes of the egg with coordinate system as described above. If the aligned versions are used in the feature extraction it is recommended to align the subimages before extracting the egg content region.

EXAMPLE 1

Features Based on Spatial Autocorrelation

The idea behind these features is to measures of the longitudinal and transverse structures of the egg contents using spatial autocorrelation of the egg contents in the longitudinal and transverse direction. The longitudinal and transverse spatial autocorrelation coefficients of the egg contents are computed in the following way:

The egg subimages are aligned with the image axes and the egg content region is extracted as described above. The extracted egg content region is then downscaled to a resolution of approximately 1.4 pixels per micrometer for eggs around 60 µm in length.

The resulting downscaled egg content image, denoted I, will form the basis of the spatial autocorrelation computations, which are explained in the following.

Three copies are made of I called $I_1$, $I_2$, and $I_3$. From $I_1$, the last row and the last column of pixels are discarded (cropped away). For $I_2$, the first row and the last column of pixels are discarded. For $I_3$, the last row and the first column of pixels are discarded. This is illustrated in FIG. 10 (top).

These three images are now all of the same dimensions, which are equal to the height of I minus one and the width of I minus 1. All of the three images contain the egg content region although the region has shifted 1 pixel upwards on image $I_2$ compared to $I_1$, and one pixel to the left on image $I_3$ compared to $I_1$.

An image region called Q is now computed. It is defined to be the intersection of the three egg content regions, i.e. all pixel locations (i,j) where $I_1(i,j)$, $I_2(i,j)$, and $I_3(i,j)$ all contain a pixel from the egg content region, as illustrated in FIG. 10 (middle). This way, the image region Q covers exactly the locations where the three egg content regions overlap.

The set of pixels in $I_1$ that Q covers are called A, and similarly for $I_2$ with B, and $I_3$ with C, as illustrated in FIG. 10 (bottom). The longitudinal autocorrelation coefficient is now computed as the correlation between A and B, and the transverse autocorrelation coefficient is now computed as the correlation between A and C. The formula for this is explained in FIG. 11.

The longitudinal and transverse autocorrelation coefficients can be used directly as two separate features in the classification or they can be combined into a single feature, for instance the ratio between the two. The ratio between the two, defined as the longitudinal autocorrelation coefficient divided by the transverse autocorrelation coefficient is hereby defined as the 'longitudinal anisotropy'. A high longitudinal anisotropy corresponds to a relatively larger longitudinal autocorrelation coefficient, which indicates that the longitudinal, linear structures of the egg contents are more prevalent than the transverse, linear structures of the egg contents.

Examples of the use of these spatial autocorrelation-based features for classification are presented in the Classification section.

EXAMPLE 2

Features Based on Edge Detection

The egg subimages are aligned with the image axes and the egg content region is extracted as described above. The extracted egg content region is then downscaled to a resolution of approximately 2.8 pixels per micrometer for eggs around 60 µm in length.

The Canny edge detector is applied to the downscaled egg content region in order to locate and measure the prevalent edges of the egg contents. The standard deviation of the Gaussian filter is set to 1, and the high and low sensitivity thresholds are set to 0.15 and 0.05, respectively, although an automatic, heuristic determination of these could be used as well.

The intermediate horizontal and vertical filter responses of the edge detector are used to compute the orientation of the detected prevalent edges. This is done using the default formula as seen in equation (10.2-11) of.

A possible quantification of the measured edge structures is to compute a 'longitudinal edge count' and a 'transverse edge count' as defined in the following.

The 'longitudinal edge count' is defined to be the number of edge pixels of the egg content region that are oriented primarily 'north' or 'south'. Similarly, the 'transverse edge count' is defined to be the number of edge pixels that are oriented primarily 'east' or 'west'. Being oriented primarily in one direction is here defined to mean being oriented in that direction plus/minus a margin of 10 to 45 degrees, for instance 22.5 degrees, as illustrated in FIG. 12.

The longitudinal and transverse edge counts can be used directly as two separate features in the classification and/or they can be combined into a single feature, for instance the ratio between the two. It is suggested to use either the ratio as a single feature or use the two edge counts as two separate features.

Examples of the use of these edge detection based features for classification are presented in the Classification section.

Examples of Darkfield-Based Features

As a compliment or an alternative to the above-described features, the light-scattering behavior/properties of the egg internals under darkfield illumination can be measured and quantified in one or more ways and used as features in the classification.

The underlying idea is that the internal structures of eggs that do not contain a larva are different than the eggs that do contain a larva. The internal structures of the first group of eggs are generally not as coarse as those of the second group of eggs, and correspondingly seem to scatter the darkfield-illumination to a higher degree. A quantification of the internal scattering can therefore be used to distinguish between the two groups.

One possible way of quantifying the internal scattering under darkfield illumination is by first extracting the egg content region from the darkfield image (as opposed to extracting it from the brightfield image as in the above-presented examples) and then computing statistics of the extracted pixel intensities. One suitable statistic would be the mean scattering intensity, i.e. the mean of the extracted pixel intensities, or the median scattering intensity, but also other statistics like the standard deviation or other image moments or order statistics could be used, including a weighted average or a contrast measure.

An example of the use of a darkfield-based feature for classification is presented in the Classification section.

Figure 4:
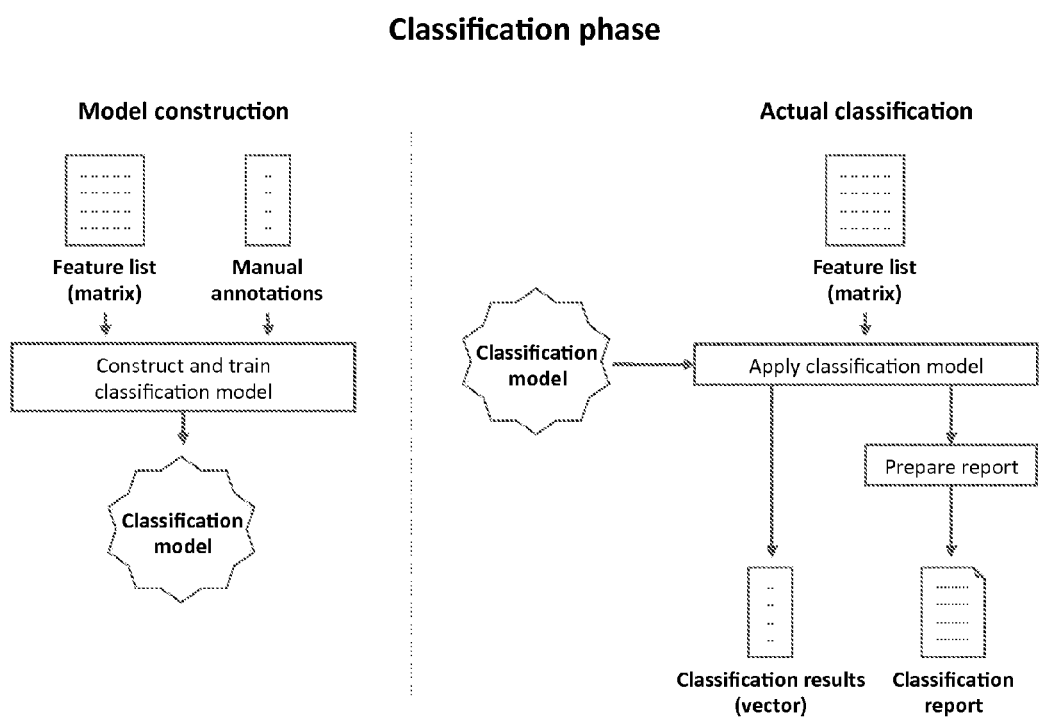
FIG. 4: Classification phase

FIG. 4: Classification Phase

The classification of *Trichuris* eggs is a statistical classification problem, also known as a supervised learning problem. The classification problem can be either binary, where each egg is classified as either containing a larva or not, or multi-class where the developmental stage of each egg is sought determined. The developmental stages are defined in the Definitions section. The classification results can be used as an indicator of the biological potency of the egg suspension.

The presented classification phase is illustrated on FIG. 4. It consists of two parts; a model construction part and an actual classification part.

The model construction part is used to build a classification model, which is later used for classifying the eggs. For the model construction, it uses an annotated dataset consisting of a feature matrix and an annotation vector. The feature matrix consists of a number of feature vectors that each correspond to an egg. Each feature vector is a row vector containing one or more features for the given egg. The annotation vector is a column vector with one value for each egg, namely the manually determined class of that egg. The manual annotation is performed by an experienced technician who is used to classify the eggs based on microscopic inspection.

The classification model is built on all or a subset of the features in the feature matrix. The number of features influences the choice of classification method. There exist a plethora of classification methods and algorithms, from k-nearest neighbor classification via linear and quadratic classifiers to decision trees, supper vector machines and neural networks, just to name some of the common approaches. The choice of algorithm is not important in this context, so a simple threshold or a linear discriminant analysis is used in the examples later.

In the actual classification part of the classification phase, the constructed classification model is applied to feature matrices of new sets of eggs with unknown classes. The result of a classification is a vector of assigned classes for each of the eggs. Along with results from the previous phases, the classification results are presented in a report of the analysis results. This report can include listings and images of the detected objects and their assigned categories as well as feature scores, assigned class and possibly a measure of the class assignment certainty.

Below are given some examples of classification based on some of the features that were introduced and explained in the previous section.

CLASSIFICATION EXAMPLE 1

Classification Based on the Canny Features

The presented Canny edge detection based feature resulted in two quantities; the longitudinal edge count and the transverse edge count. Besides using them separately as features, the ratio could be used as a feature as well.

Let the 'edge count ratio' be defined as the longitudinal edge count divided by the transverse edge count. A possible classification based on this feature alone is to use a single threshold value as classifier, for instance the value 1.8. All eggs with an edge count ratio above 1.8 are classified as containing a larva and the remaining are classified as not containing a larva. A graph of the edge count ratios of 100 eggs, presented in descending order, is seen on FIG. 13(*a*). Notice that for a threshold of 1.8, only a single egg out of the 100 is misclassified based on this edge count ratio feature alone.

Another way to classify the eggs is to use the longitudinal and transverse edge counts as two separate features as mentioned. A linear discriminant analysis with empirical prior probabilities could be used for this task. As seen on FIG. 13(*b*), this classification is also able to correctly classify all eggs except one.

CLASSIFICATION EXAMPLE 2

Classification Based on Longitudinal Anisotropy

In the previous section the longitudinal anisotropy was introduced as the ratio between the longitudinal, spatial autocorrelation coefficient and the transverse, spatial autocorrelation coefficient of the egg content region. Similar to the edge count features above, this feature could be used for a one-dimensional classification, or the individual correlation coefficients could be used as separate features. FIG. 14(*a*) shows a classification based on the individual correlation coefficients.

It is also possible to combine any of the above features with other features, for instance the darkfield-based mean scattering intensity, as described earlier. An example of a two-dimensional classification based on the longitudinal anisotropy and the mean scattering intensity for another dataset can be seen on FIG. 14(*b*).

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A computer vision based method for extracting features relating to the developmental stages of *Trichuris* spp. eggs, wherein for the final developmental stages a larva is present inside the egg, said *Trichuris* spp. eggs having a substantially oblong or elliptical shape with a protruding polar plug at each end, the shape of the *Trichuris* spp. eggs thereby defining a longitudinal direction and a transverse direction of the eggs, said method comprising:
   a) obtaining and storing one or more digital images of *Trichuris* spp. eggs suspended in a liquid solution,
   b) detecting one or more *Trichuris* spp. eggs in the image(s), and
   c) extracting one or more features from an egg content image region representing at least part of the egg contents of a detected egg, wherein one or more features are extracted from an egg content image region being extracted from an image or image region which includes a full representation of a detected *Trichuris* spp. egg, and
wherein the extracted egg content image region excludes the polar plugs of the detected *Trichuris* spp. egg.

2. A method according to claim 1, wherein the extracted egg content image region excludes the shell of the detected *Trichuris* spp. egg.

3. A method according to claim 2, wherein the extracted egg content image region has a substantially elliptical shape, thereby defining a content ellipse image.

4. A computer vision based method for extracting features relating to the developmental stages of *Trichuris* spp. eggs, wherein for the final developmental stages a larva is present inside the egg, said *Trichuris* spp. eggs having a substantially oblong or elliptical shape with a protruding polar plug at each end, the shape of the *Trichuris* spp. eggs thereby defining a longitudinal direction and a transverse direction of the eggs, said method comprising:
   a) obtaining and storing one or more digital images of *Trichuris* spp. eggs suspended in a liquid solution,
   b) detecting one or more *Trichuris* spp. eggs in the image(s), and
   c) extracting one or more features from an egg content image region representing at least part of the egg contents of a detected egg wherein one or more features are extracted from an egg content image region being a bright-field egg content image region, and wherein the bright-field egg content image region is extracted from a bright-field image or image region, which includes a full representation of a detected *Trichuris* spp. egg,
with the extracted egg content image region excluding the polar plugs of the detected *Trichuris* spp. egg.

5. A method according to claim 4, wherein the extracted egg content image region excludes the shell of the detected *Trichuris* spp. egg.

6. A method according to claim 5, wherein the extracted egg content image region has a substantially elliptical shape, thereby defining a content ellipse image.

7. A computer vision based method for extracting features relating to the developmental stages of *Trichuris* spp. eggs, wherein for the final developmental stages a larva is present inside the egg, said *Trichuris* spp. eggs having a substantially oblong or elliptical shape with a protruding polar plug at each end, the shape of the *Trichuris* spp. eggs thereby defining a longitudinal direction and a transverse direction of the eggs, said method comprising:
   a) obtaining and storing one or more digital images of *Trichuris* spp. eggs suspended in a liquid solution,
   b) detecting one or more *Trichuris* spp. eggs in the image(s), and
   c) extracting one or more features from an egg content image region representing at least part of the egg contents of a detected egg,
wherein the extraction of one or more features from the egg content image region includes one or more measurements of the direction-dependent structures of the egg contents.

8. A method according to claim 7, wherein the extraction of one or more features from the egg content region includes one or more measurements of the longitudinal structures of the egg contents and/or one or more measurements of the transverse structures of the egg contents.

9. A method according to claim 8, wherein the one or more measurements of the longitudinal structures are based on a measure of the linear structures and/or edge structures in the longitudinal direction.

10. A method according to claim 9, wherein the linear structures and/or edge structures are measured at a predetermined scale.

11. A method according to claim 9, wherein one or more measurements of the transverse structures are based on a measure of the linear structures and/or edge structures in the transverse direction, and wherein expressions representing a measure of the edge structures in the longitudinal and transverse directions are obtained by use of an edge detector algorithm.

12. A method according to claim 11, wherein the edge detector algorithm is selected from the following algorithms: the Canny edge detector algorithm, the Sobel edge detector algorithm, and the Prewitt edge detector algorithm.

13. A method according to claim 11, wherein the expression representing the edge structures in the longitudinal direction, longitudinal edge count, is defined as the number of edge pixels of the egg contents given by the edge detector algorithm and being oriented substantially in the longitudinal direction, and wherein the expression representing the edge structures in the transverse direction, transverse edge count, is defined as the number of edge pixels of the egg contents given by the edge detector algorithm and being oriented substantially in the transverse direction.

14. A method according to claim 13, wherein the longitudinal edge count is defined as the number of edge pixels of the egg contents given by the edge detector algorithm and being oriented in the longitudinal direction plus/minus an angle within the range of 10-45 degrees, and wherein the transverse edge count is defined as the number of edge pixels of the egg contents given by the edge detector algorithm and being oriented in the transverse direction plus/minus an angle within the range of 10-45 degrees.

15. A method according to claim 8, wherein one or more measurements of the transverse structures are based on a measure of the linear structures and/or edge structures in the transverse direction.

16. A method according to claim 15, wherein the linear structures and/or edge structures are measured at a predetermined scale.

17. A method according to claim 8, wherein the one or more measurements of the longitudinal structures are based on a measure of the linear structures and/or edge structures in the longitudinal direction at one or more scales in a multi-scale representation of the image region from which the features are extracted.

18. A method according to claim 17, wherein the multi-scale representation of the image region from which the features are extracted is a pyramid representation or a scale space representation.

19. A method according to claim 8, wherein one or more measurements of the transverse structures are based on a measure of the linear structures and/or edge structures in the transverse direction at one or more scales in a multi-scale representation of the image region from which the features are extracted.

20. A method according to claim 19, wherein the multi-scale representation of the image region from which the features are extracted is a pyramid representation or a scale space representation.

21. A method according to claim 8, wherein one or more measurements of the longitudinal structures of the egg contents is based on a longitudinal comparison of pixels intensities obtained from similarly addressed pixels in first and second image parts representing at least part of the egg contents of a detected egg, with the second image part being obtained by shifting the first image part one or more pixels in a direction substantially following the longitudinal direction of the egg.

22. A method according to claim 21, wherein one or more measurements of the transverse structures of the egg contents is based on
a transverse comparison of pixel intensities obtained from similarly addressed pixels in the first image part and a third image part representing at least part of the egg contents of a detected egg, with the third image part being obtained by shifting the first image part one or more pixels in a direction substantially following the transverse direction of the egg, and wherein
the longitudinal comparison of pixel intensities from the first and second image parts comprises calculating a longitudinal correlation coefficient $\rho_{long}$ for pixel intensities representing at least part of the similarly addressed pixels, and wherein the transverse comparison of pixel intensities from the first and third image parts comprises calculating a transverse correlation coefficient $\rho_{trans}$ for pixel intensities representing at least part of the similarly addressed pixels.

23. A method according to claim 22, wherein the feature extraction further includes a ratio measure based on the ratio between the longitudinal correlation coefficient $\rho_{long}$ and the transverse correlation coefficient $\rho_{trans}$.

24. A method according to claim 8, wherein one or more measurements of the transverse structures of the egg contents is based on a transverse comparison of pixel intensities obtained from similarly addressed pixels in the first image part and a third image part representing at least part of the egg contents of a detected egg, with the third image part being obtained by shifting the first image part one or more pixels in a direction substantially following the transverse direction of the egg.

25. A computer vision based method for extracting features relating to the developmental stages of Trichuris spp. eggs, wherein for the final developmental stages a larva is present inside the egg, said Trichuris spp. eggs having a substantially oblong or elliptical shape with a protruding polar plug at each end, the shape of the Trichuris spp. eggs thereby defining a longitudinal direction and a transverse direction of the eggs, said method comprising:
a) obtaining and storing one or more digital images of Trichuris spp. eggs suspended in a liquid solution, the stored digital images of the Trichuris spp. eggs comprising one or more dark-field images,
b) detecting one or more Trichuris spp. eggs in the image(s), and
c) extracting one or more features from an egg content image region representing at least part of the egg contents of a detected egg,
wherein one or more features are extracted from an egg content image region being a dark-field egg content image region.

26. A method according to claim 25, wherein one or more features are extracted from a dark-field egg content image region being extracted from a dark-field image region which includes a full representation of a detected Trichuris spp. egg.

27. A method according to claim 26, wherein the extracted dark-field egg content image region excludes the polar plugs of the detected Trichuris spp. egg.

28. A method according to claim 27, wherein the extracted dark-field egg content image region excludes the shell of the detected Trichuris spp. egg.

29. A method according to claim 28, wherein the extracted dark-field egg content image region has a substantially elliptical shape, thereby defining a content ellipse image.

30. A method according to claim 26, wherein the dark-field feature extraction is based on variations in pixel intensities measured or extracted for at least part of the dark-field egg content image region.

31. A method according to claim 30, wherein the dark-field feature extraction comprises a computation of the average of the extracted pixel intensities.

32. A method according to claim 30, wherein the dark-field feature extraction comprises a computation of the mean of the extracted pixel intensities, mean scattering intensity, and/or of the median of the extracted pixel intensities, median scattering intensity.

33. A computer vision based method for extracting features relating to the developmental stages of Trichuris spp. eggs, wherein for the final developmental stages a larva is present inside the egg, said Trichuris spp. eggs having a substantially oblong or elliptical shape with a protruding polar plug at each end, the shape of the Trichuris spp. eggs thereby defining a longitudinal direction and a transverse direction of the eggs, said method comprising:
a) obtaining and storing one or more digital images of Trichuris spp. eggs suspended in a liquid solution,
b) detecting one or more Trichuris spp. eggs in the image(s),
c) extracting one or more features from an egg content image region representing at least part of the egg contents of a detected egg, and
d) classifying the detected egg based on at least part of the features extracted from the egg content image region representing the detected egg,
the classification of the detected egg is a binary classification with respect to the developmental stage of the egg.

34. A method according to claim 33, wherein the detected egg is classified as either containing a larva or not containing a larva.

35. A method according to claim 33, wherein the classification is at least partly based on extracted dark-field features.

36. A computer vision based method for extracting features relating to the developmental stages of Trichuris spp. eggs, wherein for the final developmental stages a larva is present inside the egg, said *Trichuris* spp. eggs having a substantially oblong or elliptical shape with a protruding polar plug at each end, the shape of the *Trichuris* spp. eggs thereby defining a longitudinal direction and a transverse direction of the eggs, said method comprising:
- a) obtaining and storing one or more digital images of *Trichuris* spp. eggs suspended in a liquid solution,
- b) detecting one or more *Trichuris* spp. eggs in the image(s),
- c) extracting one or more features from an egg content image region representing at least part of the egg contents of a detected egg, and
- d) classifying the detected egg based on at least part of the features extracted from the egg content image region representing the detected egg, the classification of the detected egg is a multi-class classification with respect to the developmental stage of the egg, said multi-class classification comprising at least three classes of developmental stages.

37. A computer vision based method for extracting features relating to the developmental stages of *Trichuris* spp. eggs, wherein for the final developmental stages a larva is present inside the egg, said *Trichuris* spp. eggs having a substantially oblong or elliptical shape with a protruding polar plug at each end, the shape of the *Trichuris* spp. eggs thereby defining a longitudinal direction and a transverse direction of the eggs, said method comprising:
- a) obtaining and storing one or more digital images of *Trichuris* spp. eggs suspended in a liquid solution,
- b) detecting one or more *Trichuris* spp. eggs in the image(s),
- c) extracting one or more features from an egg content image region representing at least part of the egg contents of a detected egg, and
- d) classifying the detected egg based on at least part of the features extracted from the egg content image region representing the detected egg, the classification is at least partly based on extracted features, for which features the extraction includes one or more measurements representing longitudinal structures and transverse structures of the egg contents.

38. A method according to claim 37, wherein the classification is at least partly based on a ratio measure obtained from a measure representing the longitudinal structures of the egg contents and a measure representing the transverse structures of the egg contents.

39. A method according to claim 38, wherein one or more measurements representing the longitudinal structures are based on a measure of the linear structures and/or edge structures in the longitudinal direction, and wherein one or more measurements representing the transverse structures are based on a measure of the linear structures and/or edge structures in the transverse direction.

40. A method according to claim 37, wherein a measure representing the longitudinal structures of the egg contents have to exceed a corresponding measure representing the transverse structures of the egg contents by a predetermined factor being larger than one in order to have the egg classified as containing a larva.

41. A computer vision based method for extracting features relating to the developmental stages of *Trichuris* spp. eggs, wherein for the final developmental stages a larva is present inside the egg, said *Trichuris* spp. eggs having a substantially oblong or elliptical shape with a protruding polar plug at each end, the shape of the *Trichuris* spp. eggs thereby defining a longitudinal direction and a transverse direction of the eggs, said method comprising the steps of:
- a) obtaining and storing one or more digital images of *Trichuris* spp. eggs suspended in a liquid solution on a computer,
- b) executing instructions on the computer to detect one or more *Trichuris* spp. Eggs in the image(s),
- c) executing instructions on the computer to extract one or more features from an egg content image region representing at least part of the egg contents of a detected egg, and
- d) executing instructions on the computer to determine or classify at least part of the detected egg, for which part one or more features are extracted, as containing a larva or not, or to determine the developmental stage of the egg and use the determination or classification results as an indicator of the biological potency of the egg.

42. A method according to claim 41, further comprising the step of generating a report based at least partly on the determination or classification results obtained in step d.

* * * * *